US00PP22540P2

(12) United States Plant Patent
Bédard

(10) Patent No.: US PP22,540 P2
(45) Date of Patent: Mar. 6, 2012

(54) FLORIBUNDA ROSE PLANT NAMED 'WEKDIDUSINRA'

(50) Latin Name: *Rosa hybrida*
Varietal Denomination: WEKdidusinra

(75) Inventor: Christian Bédard, Brea, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/925,448

(22) Filed: Oct. 20, 2010

(51) Int. Cl.
*A01H 5/00* (2006.01)

(52) U.S. Cl. ..... Plt./145

(58) Field of Classification Search ..... Plt./145, Plt./144
See application file for complete search history.

*Primary Examiner* — June Hwu

(57) ABSTRACT

A new variety of Floribunda rose suitable for garden decoration, having flowers of lemon cream coloration.

1 Drawing Sheet

Classification: The present invention relates to a new *Rosa hybrida* plant.

Variety denomination: The new plant has the varietal denomination 'WEKdidusinra'.

BACKGROUND OF THE INVENTION

This invention relates to a new and distinct variety of Floribunda Rose. It has as its seed parent the variety known as Distant Drums (not patented) and as its pollen parent the variety known as 'MACivy' (U.S. Plant Pat. No. 8,362).

SUMMARY OF THE INVENTION

Among the features which distinguish the new variety from other presently available and commercial rose cultivars known to the inventor are the following combinations of characteristics: its strong licorice flower fragrance, its lemon cream flower coloration that last throughout the life of the flower and its many large prickles on the major stems. The plant has an upright moderately bushy growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKdidusinra' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, Distant Drums by the following combination of characteristics: whereas 'WEKdidusinra' bears flowers of lemon cream coloration with very double petalage (about 33 to 70 petals), Distant Drums bears flowers of tan mauve blend coloration with significantly lesser petalage (about 17 to 25 petals).

The new variety may be distinguished from its pollen parent, 'MACivy' by the following combination of characteristics: whereas 'WEKdidusinra' bears flowers of lemon cream coloration with very double petalage (about 33 to 70 petals), 'MACivy' bears multi-colored flowers of apricot and red coloration with significantly lesser petalage (about 30 to 35 petals). The new variety has an upright moderately bushy growing habit (about 120 to about 150 cm. in height), whereas the pollen parent has an upright compact significantly shorter growing habit(about 100 to about 120 cm. in height).

COMPARISON WITH THE CLOSEST COMMERCIALLY AVAILABLE CULTIVAR

The new variety may be distinguished from its closest commercially available cultivar, 'DICappeal' (not patented) by the following combination of characteristics: whereas 'WEKdidusinra' bears flowers of lemon cream coloration with very double petalage (about 33 to 70 petals), 'DICappeal' bears flowers of chartreuse white coloration with significantly lesser petalage (about 17 to 25 petals).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in somewhat irregular rounded clusters on strong short to medium length stems (about 15 to about 50 cm.). Outdoors, the plant blooms abundantly and nearly continuously during the growing season. The flowers have a strong licorice fragrance.

BUD

The peduncle is about 2.8 to about 5.8 cm. in length, of average caliper (about 0.3 to about 0.4 cm. in diameter), and usually erect. It is moderately smooth, with some stipitate glands and few hairs. Peduncle color is between 146C and 143A often moderately suffused, especially on the side exposed to the sun, with between 183B and 187B.

Before the calyx breaks, the bud is about 1.2 to about 1.9 cm. in diameter at the widest point, about 1.6 to about 2.4 cm. in length, and ovoid to somewhat pointed in shape. The surface of the bud bears few foliaceous appendages and stipitate glands, usually with slender entire foliaceous parts extending beyond the tip of the bud about ½ or more of its length. Bud color is between 146B and 143B often lightly suffused, especially on the side exposed to the sun, with between 187B and 187A.

The sepals are about 2.0 to about 3.8 cm. in length and about 0.6 to about 1.1 cm. in width at the widest point. The outer surface color of the sepal is between 146B and 143B often lightly suffused, especially on the side exposed to the sun, with between 187B and 187A. The inner surface color of the sepal is near 146C broadly bordered by near 137A. The inner surface of the sepal is covered with fine wooly tomentum; sepal margins are lined with some stipitate glands and hairs.

The receptacle of the flower is of moderately short length (about 0.4 to about 0.5 cm.) and average in caliper (about 0.8 to about 1.0 cm. in diameter). The receptacle is cup-shaped in form. Its surface is very smooth with some hairs and with moderately thin fleshy walls. The receptacle color is between 144A and 143B.

As the petals open (after the calyx breaks), the bud is about 1.8 to about 2.4 cm. in diameter at the widest point, about 2.3 to about 2.9 cm. in length, and ovoid in form. The color of the under surfaces of the newly opened petals is between 10A and 15D. There is no visible change in coloration at the point where the petal attaches. The color of the upper surfaces of the newly opened petals is between 7D and 15D. There is no visible change in coloration at the point where the petal attaches.

BLOOM

When fully open, the bloom ranges from about 9.2 to about 10.6 cm. in diameter. Petalage is very double with about 33 to 70 petals and about 6 to 12 petaloids irregularly arranged. When partially open, the bloom form is cupped to somewhat high centered, and the petals are tightly spiraled to cupped with petal edges somewhat reflexed outward. When fully open, the bloom form is more cupped, and the petals are loosely cupped to undulated with petal edges somewhat reflexed outward and sometimes somewhat reflexed inward.

PETALS

The substance of the petals is moderately heavy and of medium thickness, with upper surfaces moderately satiny to somewhat shiny and under surfaces matte to slightly shiny. The petals are about 1.1 to about 5.7 cm. in length and about 0.8 to about 5.4 cm. in width at the widest point. Petal margins are entire.

The outer petals are moderately obovate in shape with rounded apices.

The inner petals are obovate in shape with rounded apices.

Petaloids are about 0.6 to about 2.3 cm. in length and about 0.5 to about 1.3 cm. in width at the widest point. Petaloids are irregularly shaped moderately obovate to somewhat subulate with rounded apices.

NEWLY OPENED FLOWER

The color at the base of the under surfaces of the outer petals is between 10A and 8B gradually diffusing toward the edge of the petals with between 155A and lighter than 4D. There is no visible change in coloration at the point where the petal attaches. The color at the base of the upper surfaces of the outer petals is between 6D and 10C gradually diffusing toward the edge of the petals with between 155A and lighter than 4D. At the point where the petal attaches, there is a moderately small zone of between 12A and 13B.

The under surface color of the intermediate and inner petals is between 10C and lighter than 4D. The upper surface color of the intermediate and inner petals is between 6D and lighter than 4D.

The under and upper surface colors of the petaloids are similar in coloration to the upper and under surfaces of the intermediate and inner petals.

The general tonality of the newly opened flower is between 6D and lighter than 4D.

THREE-DAY-OLD FLOWER

The color at the base of the under surfaces of the outer, intermediate and inner petals is between 4C and 5D gradually diffusing toward the edge of the petals with between 155A and 155B. At the point where the petal attaches, there is a small zone of near 12B. The color at the base of the upper surfaces of the outer, intermediate and inner petals is between lighter than 6D and 11A gradually diffusing toward the edge of the petals with between 155A and 155B. At the point where the petal attaches, there is a moderately small zone of between 12B and 13C.

The under and upper surface colors of the petaloids are similar in coloration to the upper and under surfaces of the intermediate and inner petals.

The general tonality of the three-day-old flower is between lighter than 6D and 11A at the base gradually diffusing toward the edge of the petals with between 155A and 155B.

On the spent bloom, the petals usually drop off cleanly.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 105) and are arranged regularly about the pistils; a few are mixed with petaloids. The filaments are of medium length (about 0.4 to about 1.2 cm.) most with anthers. Filaments are between 13A and 14A in color. The anthers are moderately small for the class and all open approximately at the same time. Anther color when immature is near 23B on the external part and near 16D on the internal part. Anther color at maturity is near 200D on the external part and near 200A on the internal part. Pollen is abundant and between 16C and 17D in color.

FEMALE REPRODUCTIVE ORGANS

Pistils vary in number (average about 110). The styles are moderately even, average in length (about 0.3 to about 0.7 cm.), somewhat thin in caliper, and separated to somewhat columnar. Stigma color is between 13C and 14C. Style color is between 5D and 3D often heavily suffused with between 53A and 53B. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 7.5 to about 12.6 cm. in length and about 6.4 to about 9.7 cm. in width at the widest point, moderately leathery to somewhat crisp in texture, and glossy in finish on the upper side and semi-glossy in finish on the under side. The terminal leaflets are about 3.4 to about 5.4 cm. in length and about 2.6 to about 4.2 cm. in width at the widest point, shaped moderately ovate to somewhat oval with acute apices and rounded bases. Their margins are usually simply serrate.

The upper surface color of the mature leaf is between 139A and 137A. The under surface color of the mature leaf is between 146A and 146B. The upper surface color of the young leaf is between 147A and 137A, often heavily suffused with between 187A and 183A. The under surface color of the young leaf is between 146B and 144A, often heavily suffused with between 183A and 185A.

The rachis is somewhat light to average in caliper and very rough. The upper side is moderately grooved with few hairs and some stipitate glands on the edges of the grooves. The under side of the rachis is very rough with few stipitate glands and some small prickles. The rachis color is near 146B on the under side and near 137A on the upper side often moderately suffused especially on the young leaf with between 187B and 185A.

The stipules are about 1.0 to about 1.6 cm. in length and moderately wide (about 0.6 to about 0.9 cm.) with long straight points that usually turn out at an angle of more than 45 degrees and sometimes recurve toward the stem. The stipule color is between 137A and 139A often moderately suffused especially on the young leaf with between 187C and 185A.

The petiole is somewhat light to average in caliper and very rough. The upper side is moderately grooved with few hairs and some stipitate glands on the edges of the grooves. The under side of the petiole is very rough with few stipitate glands and some small prickles. The petiole is about 0.4 to about 1.2 cm. in length and about 0.1 to about 0.15 cm in width at the widest point. The petiole color is near 146B on the under side and near 137A on the upper side often moderately suffused especially on the young leaf with between 187B and 185A.

The plant displays an average degree of resistance to powdery mildew and rust as compared to other commercial varieties grown under comparable conditions in Pomona, Calif. The plant's winter hardiness and drought/heat tolerance are yet to be determined.

GROWTH

The plant has an upright moderately bushy medium height growing habit (about 120 to about 150 cm. in height and about 46 to about 58 cm. spread at the widest point), with very full branching. It displays vigorous growth and the canes are of somewhat heavy caliper for the class (about 1.4 to about 1.9 cm. in width at the widest point).

The color of the major stems is between 147B and 146C. They bear many large prickles that are about 0.9 to about 1.2 cm. in length. The large prickles are angled moderately downward with a medium length broad oval base; prickle color is between 165A and 200D. The major stem bears few small prickles of similar shape and coloration.

The color of the branches is between 146B and 146C. They bear some large prickles which are of similar shape to the large prickles on the major stems. The large prickles are about 0.5 to about 0.7 cm. in length. Prickle color is near 160A sometimes lightly suffused with near 53B. The branches bear few small prickles of similar shape and coloration.

The color of the new shoots is between 146C and 146D often heavily suffused with between 187B and 183A. They bear some large prickles which are of similar size and shape to the large prickles on the branches; prickle color is between 152B and 152C often heavily suffused with between 187C and 53B. The shoots bear few small prickles of similar shape and coloration.

I claim:

1. A new and distinct Floribunda rose plant of the variety substantially as described and illustrated herein.

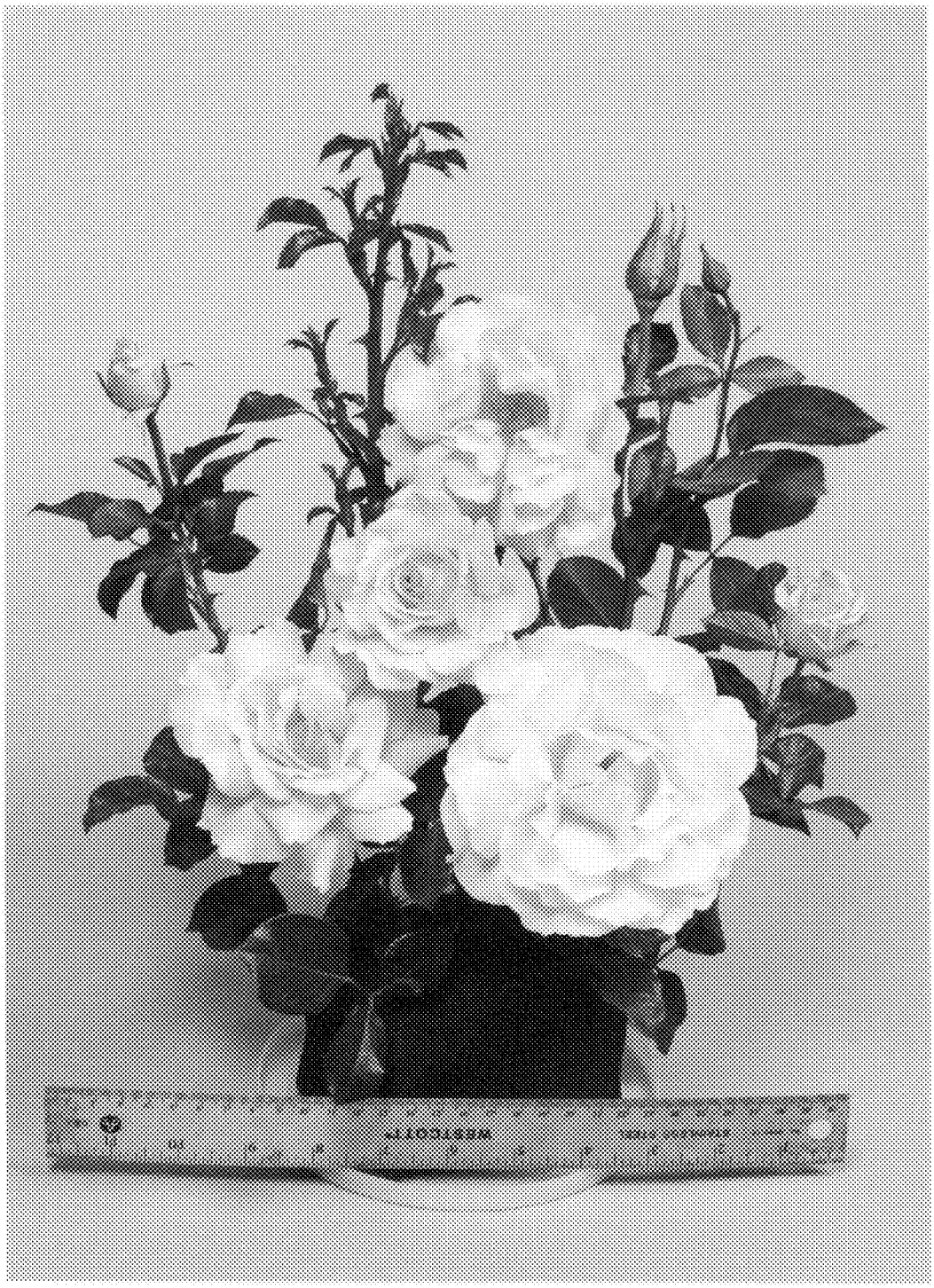

* * * * *